(12) United States Patent
Mann et al.

(10) Patent No.: US 6,686,468 B2
(45) Date of Patent: Feb. 3, 2004

(54) H-ANNELLATED BENZO[F]CHROMENES

(75) Inventors: Claudia Mann, Munich (DE); Manfred Melzig, Wessling (DE); Udo Weigand, Munich (DE)

(73) Assignee: Optische Werke G. Rodenstock, Munich (DE)

( * ) Notice: Subject to any disclaimer, the term of this patent is extended or adjusted under 35 U.S.C. 154(b) by 25 days.

(21) Appl. No.: 10/129,736

(22) PCT Filed: Jul. 24, 2001

(86) PCT No.: PCT/EP01/08557

§ 371 (c)(1),
(2), (4) Date: May 10, 2002

(87) PCT Pub. No.: WO02/22594

PCT Pub. Date: Mar. 21, 2002

(65) Prior Publication Data

US 2003/0040623 A1 Feb. 27, 2003

(51) Int. Cl.⁷ .............................................. C07D 413/00
(52) U.S. Cl. ........................ 544/150; 544/111; 252/586; 546/196

(58) Field of Search ................................. 544/150, 111; 546/196; 252/586

(56) References Cited

U.S. PATENT DOCUMENTS

| | | | |
|---|---|---|---|
| 3,567,605 A | 3/1971 | Becker | 204/158 |
| 5,869,658 A | 2/1999 | Lin et al. | 544/106 |
| 6,022,495 A | 2/2000 | Kumar | 252/586 |

FOREIGN PATENT DOCUMENTS

| | | |
|---|---|---|
| WO | WO 99/23071 | 5/1999 |
| WO | WO 01/36406 | 5/2001 |

*Primary Examiner*—Amelia Owens
(74) *Attorney, Agent, or Firm*—Crowell & Moring LLP

(57) ABSTRACT

The present invention relates to specific photochromic h-annellated benzo[f]chromene derivatives and their use in synthetic resins of all types, especially for ophthalmic applications. In particular, the present invention relates to photochromic compounds derived from benzo[f]chromenes, which in the open form have especially long-wave absorption maxima making it possible to obtain violet to blue tints when used in phototropic glasses.

12 Claims, 2 Drawing Sheets

Figure 1:
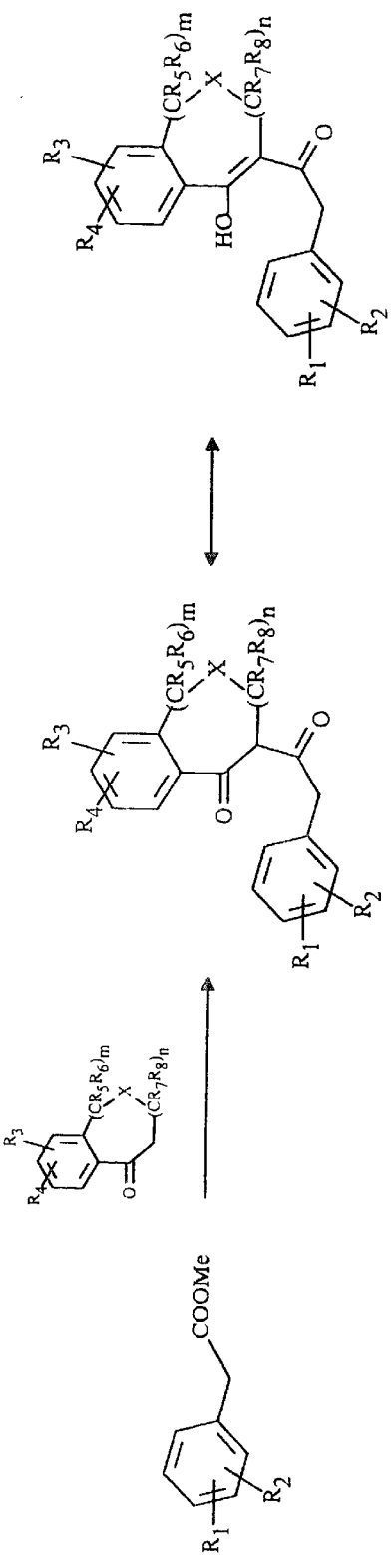
Figure 1:
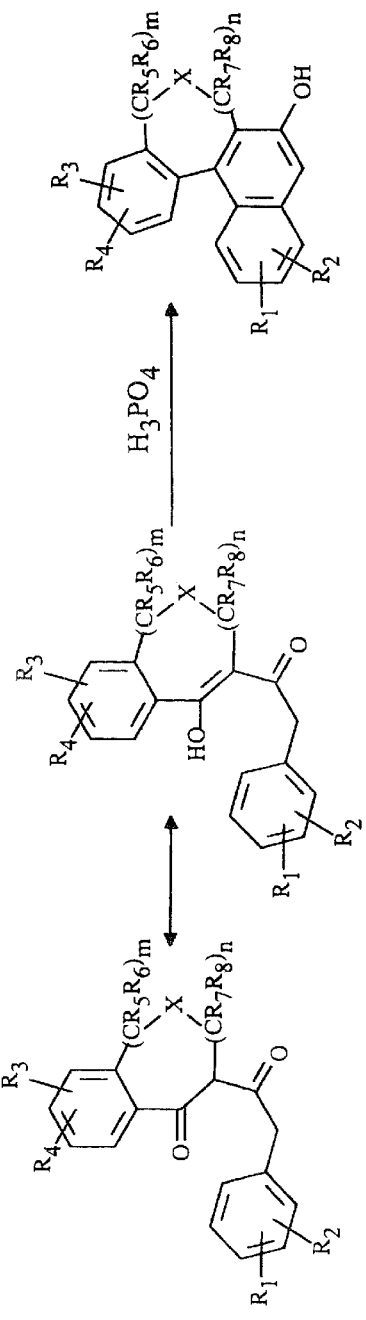
Figure 1:
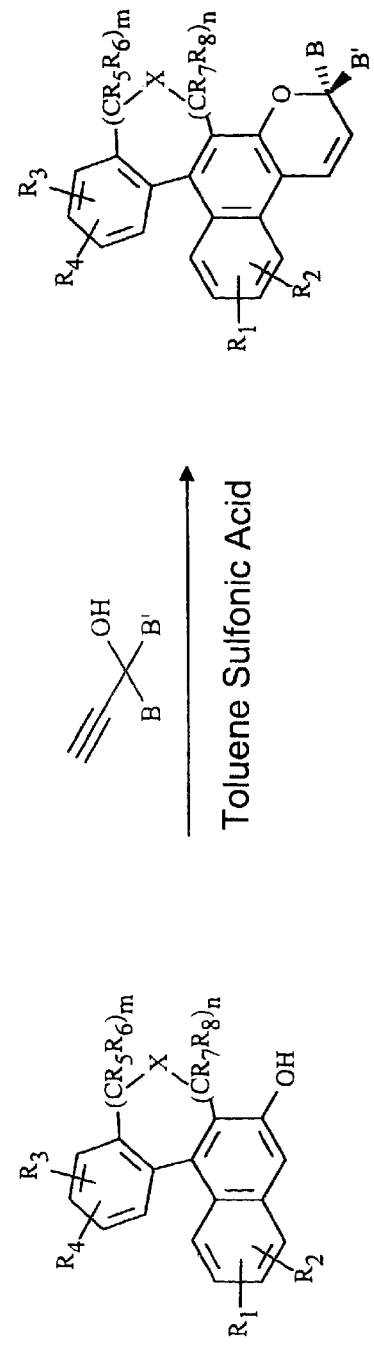

Reaction Scheme i) Ester condensation ii) Intramolecular cyclization iii) Protection of naphthol-OH  ----->  -OSi$^t$BuPh$_2$ iv) Conversion of R$^1$ and/or R$^2$ from e.g. Br to NR'R'' by Pd –catalyzed addition v) Elimination of the naphthol-OH protective group vi) Condensation

H-ANNELLATED BENZO[F]CHROMENES

The present invention relates to specific photochromic h-annellated benzo[f]chromene derivatives and their use in synthetic resins of all types, especially for ophthalmic applications. In particular, the present invention relates to photochromic compounds derived from benzo[f]chromenes, which in their open form have particularly long-wave absorption maxima making it possible to achieve violet to blue tints if used in phototropic glasses.

Various classes of dyes that reversibly change their color when irradiated with light of certain wavelengths, particularly sunlight, are known in the art. This is due to the fact that these dye molecules change into an excited colored state when supplied with energy in the form of light. When the energy supply is interrupted, they leave this state again and return to their colorless or at least hardly colored normal state. These photochromic dyes include, for instance, the naphthopyrans, which have already been described in the prior art with various substituents.

Pyrans, especially naphthopyrans and larger ring systems derived therefrom are photochromic compounds that even today are the subject of intensive investigations. Although a patent application was filed for them as early as 1966 (U.S. Pat. No. 3,567,605), it was not until the nineties that compounds that appeared suitable for use in eyeglasses were developed.

On the one hand, the prior art dyes frequently do not have sufficiently long-wave absorption in the excited or in the unexcited state. This causes problems also in combinations with other photochromic dyes. On the other hand, they are also often excessively temperature sensitive with respect to darkening and brightening is simultaneously too slow. In addition, the described dyes have an insufficiently long service life. Consequently, this type of sunglasses is not sufficiently durable. The latter is noticeable in their rapidly deteriorating performance and/or strong yellowing.

3H-naphthopyrans derived from 2-naphthols and their higher analog derivatives derived therefrom by annellation are a group of photochromic dyes whose longest-wave absorption maximum in the excited form is primarily in the spectral range of 420 nm to 500 nm. As a result they give a yellow, orange or red color impression (see U.S. Pat. No. 5,869,658 and U.S. Pat. No. 6,022,495). For neutrally darkening phototropic glasses, however, powerful violet to blue photochromic dyes are required. Violet to blue photochromic dyes that are currently available in the prior art stem from the class of the spiroxazines, fulgides or 2H-naphtho[1,2-b]pyrans. Spiroxazine dyes, however, are typically disadvantageous with respect to their high-temperature performance, while fulgide dyes do not have satisfactory properties for use in sunglasses regarding their service life and 2H-naphtho[1,2-b]pyrans regarding their brightening rate.

Thus, the object of the present invention is to provide novel photochromic dyes with improved properties compared to the compounds described in the prior art. Compared to comparable prior art compounds, the photochromic compounds are to be distinguished especially by longer-wave absorption in the excited state and at the same time are to exhibit good kinetic and service life properties, i.e., faster brightening rates and good behavior in the durability test.

This object is attained by the subjects characterized in the claims.

Specifically provided are photochromic h-annellated benzo[f]chromenes having the general formula (I):

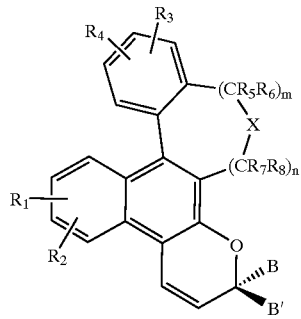

(I)

where
n and m independently represent 0, 1 or 2,
the radicals $R_1$, $R_2$, $R_3$ and $R_4$ each independently represent a substituent selected from
the group α consisting of a hydrogen atom, a ($C_1$–$C_6$) alkyl radical, a ($C_3$–$C_7$) cycloalkyl radical, which can have one or more heteroatoms, a ($C_1$–$C_6$) alkoxy radical, a hydroxy group, a trifluoromethyl group, bromine, chlorine and fluorine; the group β consisting of an unsubstituted, monosubstituted or disubstituted phenyl, phenoxy, benzyl, benzyloxy, naphthyl or naphthoxy radical, wherein the substituents may be selected from the group α and phenyl;
the group χ wherein the radicals $R_1$ and $R_2$ or $R_3$ and $R_4$ each form an —A—$(CH_2)_k$—B— group bound to the aromatic ring where k=1 or 2, wherein A and B independently are selected from oxygen, sulfur, $CH_2$, $C(CH_3)_2$ or $C(C_6H_5)_2$, and wherein a benzo ring may in turn be annellated to said —A—$(CH_2)_k$—B— group;
the group δ consisting of an unsubstituted, monosubstituted or disubstituted amino group, wherein the amine substituents may be selected from a ($C_1$–$C_6$) alkyl radical, a ($C_3$–$C_7$) cycloalkyl radical, a phenyl or benzyl radical unsubstituted or substituted with one or more substituents from the group α, an N-morpholine group, an N-thiomorpholine group, an N-piperidine group, an N-azacycloheptane group, an N-piperazine group, an N-(N'-($C_1$–$C_6$-alkyl)piperazine group, an N-pyrrolidine group, an N-imidazolidine group, an N-pyrazolidine group, an N-aziridine group, an N-azetidine group, an N-indoline group, an N-carbazole group, an N-phenothiazine group, an N-phenazine group, an N-phenoxazine group, an N-tetrahydroquinoline group, and an N-tetrahydroisoquinoline group,
the group ε, wherein the radicals $R_1$ and $R_2$, i.e., $R_1/R_2$, or $R_3$ and $R_4$, i.e., $R_3/R_4$, respectively, together form a —D—$(CH_2)_k$—E— group bound to the benzo ring where k=1 or 2, wherein independently D is selected from $N(CH_3)$ or $N(C_6H_5)$ and E from oxygen, sulfur, $CH_2$, $C(CH_3)_2$, $C(C_6H_5)_2$, $N(CH_3)$ or $N(C_6H_5)$, and wherein a benzo ring may in turn be annellated to this —D—$(CH_2)_k$—E— group, or
the group φ wherein the radicals $R_1$ and $R_2$ or $R_3$ and $R_4$, respectively, form a julolidinyl unit together with the benzene ring to which they are bound,
provided that within the radicals $R_1$, $R_2$, $R_3$ and $R_4$ or within $R_1/R_2$ and $R_3/R_4$ at least one is selected from the aforementioned groups δ, ε and φ, i.e., at least one of the radicals $R_1$, $R_2$, $R_3$ and $R_4$ or $R_1/R_2$ and $R_3/R_4$ is an electron-donating substituent from the class of the nitrogen donor substituents;

the radicals $R_5$, $R_6$, $R_7$ and $R_8$, respectively, independently are selected from the group α and phenyl, or the radicals $R_5$ and $R_6$ together with the radical $R_3$ of the directly adjacent benzo ring form an unsubstituted, monosubstituted or disubstituted benzo or pyrido ring annellated thereto, whose substituents may be selected from the group α and phenyl, or, if m or n is 2, the directly adjacent radicals $R_5$ and $R_6$ of two adjacent $CR_5R_6$ units or the directly adjacent radicals $R_7$ and $R_8$ of two adjacent $CR_7R_8$ units together form an annellated, unsubstituted, monosubstituted or disubstituted benzo or pyrido ring whose substituents may be selected from the group α and phenyl, or the radicals $R_5$ and $R_6$ and/or the radicals $R_7$ and $R_8$ together represent a $(C_3-C_7)$ cycloalkyl radical, which can have one or more heteroatoms, such as, for instance, oxygen, nitrogen or sulfur, wherein a benzo ring may be annellated to this cycloalkyl radical;

X is selected from O, S, $CR_9R_{10}$ or $NR_{11}$, wherein the radical $R_{11}$ can be hydrogen, cyano, $(C_1-C_6)$ alkyl, $(C_3-C_7)$ cycloalkyl or phenyl, and the radicals $R_9$ and $R_{10}$ independently are selected from the group α and phenyl, or the radicals $R_9$ and $R_{10}$ together represent a $(C_3-C_7)$ cycloalkyl radical, which can have one or more heteroatoms, or, if X is $CR_9R_{10}$, the radicals $R_9$ and $R_{10}$ together with the radicals $R_5$ and $R_6$ or $R_7$ and $R_8$ of a directly adjacent $CR_5R_6$ unit or $CR_7R_8$ unit can also stand for an unsubstituted, monosubstituted or disubstituted benzo or pyrido ring annellated to the $X-C(R_5R_6)$ or $X-C(R_7R_8)$ bond whose substituents may be selected from the group α and phenyl;

B and B' independently are selected from one of the following groups a), b), c) or d), wherein they
   a) are monosubstituted, disubstituted or trisubstituted aryl radicals wherein the aryl radical is phenyl or naphthyl;
   b) are unsubstituted, monosubstituted and disubstituted heteroaryl radicals, wherein the heteroaryl radical is pyridyl, furanyl, benzofuran-2-yl, benzofuran-3-yl, thienyl, benzothieno-2-yl, benzothieno-3-yl, or julolidinyl; wherein the substituents of the aryl or the heteroaryl radicals in a) and b) are those selected from the groups α, β or δ or two directly adjacent substituents together can form a $—D—(CH_2)_k—E—$ group bound to the benzo ring as defined above, i.e., k stands for 1 or 2 and independently D stands for $—N(CH_3)$ or $—N(C_6H_5)$ and E for oxygen, sulfur, $CH_2$, $C(CH_3)_2$, $C(C_6H_5)_2$, $—N(CH_3)$ or $—N(C_6H_5)$, and a benzo ring can in turn be annellated to this $—D—(CH_2)_k—E—$ group;
   c) are structural units having the following formulas (V) and (W):

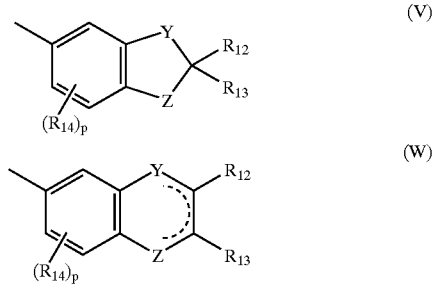

where
   Y and Z independently are O, S, CH, $CH_2$ or $NR_{11}$, wherein the radical $R_{11}$ is as defined above, the radicals $R_{12}$ and $R_{13}$ independently represent hydrogen and/or a $(C_1-C_6)$ alkyl radical and the radical $R_{14}$ is a substituent from the group α, wherein p is 1, 2, or 3, provided that, if Y in formula (V) is $NR_{11}$, Z is carbon, or
   d) B and B' together form an unsubstituted, monosubstituted or disubstituted fluorene-9-ylidene radical or a saturated hydrocarbon radical, which is $C_3-C_{12}$ spiro-monocyclic, $C_7-C_{12}$ spiro-bicyclic and/or $C_7-C_{12}$ spiro-tricyclic wherein the fluorene substituents are selected from the group α.

According to the present invention, through h-annellation of benzo[f]chromene systems, compounds are provided whose photochromic properties have advantages compared to the compounds known in the prior art. In particular, the compounds according to the invention have especially long-wave absorption maxima in the open (colored) form, so that for the first time violet to blue tints can be obtained for benzo[f]chromene systems (nomenclature according to IUPAC; other name: 3H-naphtho[1,2-b]pyrans). At the same time, the inventive photochromic h-annellated benzo[f]chromene derivatives have comparable kinetic and service life properties compared to corresponding compounds from the prior art, i.e., rapid brightening rate and good behavior in the durability test.

FIG. 1 shows a synthesis pathway to prepare exemplary photochromic compounds according to the invention.

The cycle or heterocycle annellated in the h-position of the benzo[f]chromene system is preferably a five-membered ring (n=m=0), a six-membered ring (n=1, m=0 or m=1, n=0) or a seven-membered ring (with preferably n=m=1).

Preferred photochromic h-annellated benzo[f]chromene derivatives according to the present invention have the following general formula (II) or (III):

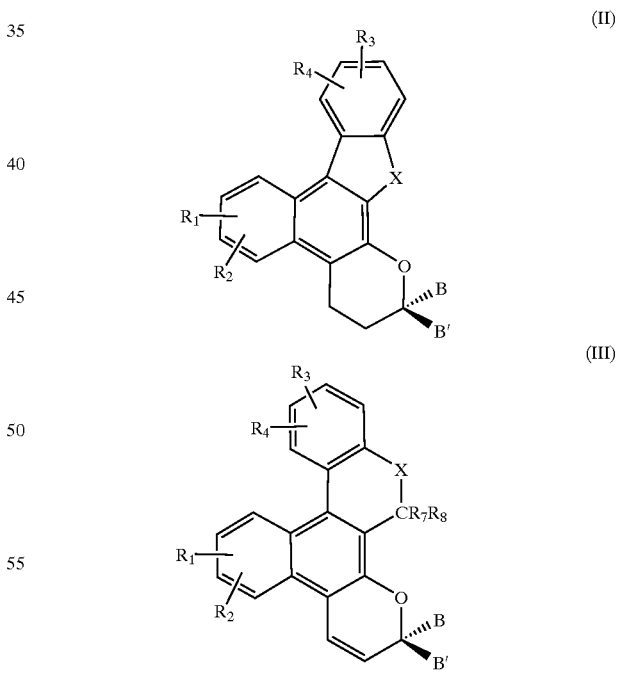

where B, B', $R_1$, $R_2$, $R_3$, $R_4$, $R_7$, $R_8$ and X are defined as above.

Preferably, the radicals $R_1$, $R_2$, $R_3$ and $R_4$ according to the above formulas (I), (II) or (III) are selected from the groups α, β and δ, provided that within the radicals $R_1$, $R_2$, $R_3$ and $R_4$ at least one is selected from the aforementioned group δ. Particularly preferably, at least one of the radicals $R_1$ and $R_2$ is selected from the group δ. Particularly preferably at least one of the radicals $R_1$ and $R_2$ is selected from the group δ. Still more preferably, the radical $R^1$ is selected from the group δ, wherein the radical $R_1$ is bound in the 7-position of the h-annellated 2H-benzo[f]chromene system. Within the group δ, an unsubstituted, monosubstituted or disubstituted amino group is particularly preferred, wherein the amine substituents may be selected from a ($C_1$–$C_6$) alkyl radical, a ($C_3$–$C_7$) cycloalkyl radical, a phenyl or benzyl radical unsubstituted or substituted with one or more substituents of the group α, an N-morpholine group, an N-piperidine group, an N-azacycloheptane group, an N-piperazine group, an N-(N'-($C_1$–$C_6$-alkyl) piperazine group, an N-pyrrolidine group, an N-imidazolidine group and an N-pyrazolidine group.

The radicals $R_5$, $R_6$, $R_7$ and $R_8$ each independently are selected from preferably the group α. X can especially be O, $CR_9R_{10}$ or $NR_{11}$, wherein the radicals $R_9$, $R_{10}$ and $R_{11}$ are defined as above. If X stands for $CR_9R_{10}$, the groups $R_9$ and $R_{10}$ together can especially stand for a ($C_3$–$C_7$) cycloalkyl radical, which can have one or more heteroatoms.

In a particularly preferred embodiment, B and B' in the above formulas (I) or (II) and (III) independently are monosubstituted, disubstituted and trisubstituted aryl radicals, wherein the aryl radical respectively is a phenyl radical or a naphthyl radical.

If the radicals $R_1$ and $R_2$ or $R_3$ and $R_4$, respectively, form a julolidinyl unit together with the benzene ring to which they are bound, i.e., with the benzo ring annellated in the f-position to the 2H-chromene unit, the following structural unit results:

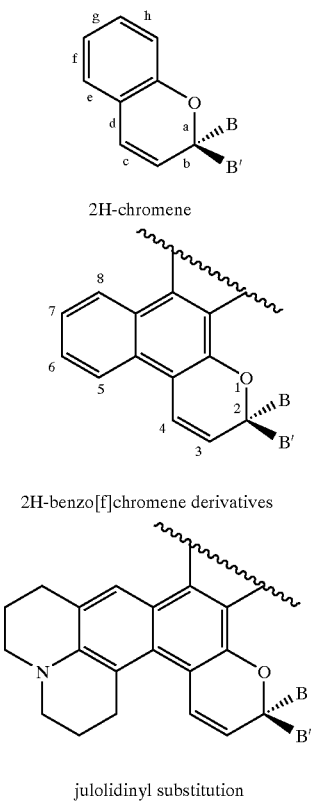

2H-chromene 2H-benzo[f]chromene derivatives julolidinyl substitution

To be cited as the —A—$(CH_2)_k$—B— unit is especially —O—$(CH_2)_2$—O—, wherein a benzo cycle is possibly annellated to the ethylene group thereof. To be cited as the —D—$(CH_2)_k$—E— unit are, in particular:

—NMe—$(CH_2)_2$—NMe—, —NPh—$(CH_2)_2$—NPh—, —NMe—$(CH_2)_2$—O—, NPh—$(CH_2)_2$—NMe—, and —NMe—$(CH_2)_2$—C$(CH_3)_2$—.

The —A—$(CH_2)_k$—B— unit or the —D—$(CH_2)_k$—E— unit is bound to the respective benzo ring via A and B or D and E ortho to one another.

Particularly preferred photochromic h-annellated benzo[f]chromene derivatives according to the present invention are:

(1) 7-dimethylamino-6-methoxy-2-(4-(N-morpholinyl)phenyl)-2-phenyl-2H,13H-indeno[1,2-h]benzo[f]chromene, (2) 7-dimethylamino-6-methoxy-2-(4-(N-morpholinyl)phenyl)-2,13,13-triphenyl-2H,13H-indeno[1,2-h]benzo[f]chromene, (3) 7-dimethylamino-6-methoxy-2-(4-(N-morpholinyl)phenyl)-2-phenyl-2H-13,14-dihydro-naphtho[1,2-h]benzo[f]chromene, (4) 7-dimethylamino-6-methoxy-2-(4-(N-morpholinyl)phenyl)-2-phenyl-2H-benzofuro[3,2-h]benzo[f]chromene, (5) 2-(4-dimethylaminophenyl)-6-methoxy-7-(N-piperidinyl)-2-phenyl-2H,13H-indeno[1,2-h]benzo[f]chromene, (6) 2-(4-dimethylaminophenyl)-6-methoxy-7-(N-piperidinyl)-2,13,13-triphenyl-2H,13H-indeno[1,2-h]benzo[f]chromene, (7) 2-(4-dimethylaminophenyl)-6-methoxy-7-(N-piperidinyl)-2-phenyl-2H-13,14-dihydro-naphtho[1,2-h]benzo[f]chromene, (8) 2-(4-dimethylaminophenyl)-6-methoxy-7-(N-piperidinyl)-2-phenyl-2H-benzofuro[3,2-h]benzo[f]chromene, (9) 2-(4-dimethylaminophenyl)-6-methoxy-7-(N-morpholinyl)-2-phenyl-2H,13H-indeno[1,2-h]benzo[f]chromene,

(10) 2-(4-dimethylaminophenyl)-6-methoxy-7-(N-morpholinyl)-2,13,13-triphenyl-2H,13H-indeno[1,2-h]benzo[f]chromene,

(11) 2-(4-dimethylaminophenyl)-6-methoxy-7-(N-morpholinyl)-2-phenyl-2H-13,14-dihydro-naphtho[1,2-h]benzo[f]chromene,

(12) 2-(4-dimethylaminophenyl)-6-methoxy-7-(N-morpholinyl)-2-phenyl-2H-benzofuro[3,2-h]benzo[f]chromene,

(13) 7-methoxy-6-(N-morpholinyl)-2-(4-(N-morpholinyl)phenyl)-2-phenyl-2H,13H-indeno[1,2-h]benzo[f]chromene,

(14) 7-methoxy-6-(N-morpholinyl)-2-(4-(N-morpholinyl)phenyl)-2,13,13-triphenyl-2H,13H-indeno[1,2-h]benzo[f]chromene,

(15) 7-methoxy-6-(N-morpholinyl)-2-(4-(N-morpholinyl)phenyl)-2-phenyl-2H-13,14-dihydro-naphtho[1,2-h]benzo[f]chromene,

(16) 7-methoxy-6-(N-morpholinyl)-2-(4-(N-morpholinyl)phenyl)-2-phenyl-2H-benzofuro[3,2-h]benzo[f]chromene,

(17) 2-(4-dimethylaminophenyl)-9-methyl-2-phenyl-2H,9H,15H-7,8-dihydroindeno[1,2-h]benzo[1,4]oxazino[6,7-f]chromene,

(18) 2-(4-dimethylaminophenyl)-9-methyl-2,15,15-triphenyl-2H,9H,15H-7,8-dihydroindeno[1,2-h]benzo[1,4]oxazino[6,7-f]chromene,

(19) 2-(4-dimethylaminophenyl)-9-methyl-2-phenyl-2H,9H-7,8,15,16-tetrahydronaphtho[1,2-h]benzo[1,4]oxazino[6,7-f]chromene, and

(20) 2-(4-dimethylaminophenyl)-9-methyl-2-phenyl-2H, 9H-benzofuro[3,2-h]benzo[1,4]-oxazino[6,7-f]chromene.

The longest-wave absorption maxima of the open form of the aforementioned exemplary photochromic h-annellated benzo[f]chromene derivatives according to the present invention are listed in the following table by way of example.

| Compounds | Longest-wave Absorption maximum of the Open (Colored) Form |
|---|---|
| (1) – (4) | 570 – 575 nm |
| (5) – (8) | 585 – 595 nm |
| (9) – (12) | 565 – 575 nm |
| (13) – (16) | 545 – 555 nm |
| (17) – (20) | 590 – 600 nm |

The compounds according to the invention can be used in synthetic resin materials or synthetic resin objects of any type and shape for a wide variety of applications where photochromic behavior is important. It is possible to use one dye according to the present invention or a mixture of such dyes. For example, the inventive photochromic benzo[f] chromene dyes may be used in lenses, particularly ophthalmic lenses, lenses for eyeglasses of all types, e.g., ski goggles, sunglasses, motor cycle goggles, visors for protective helmets and the like. The inventive photochromic benzo[f]chromene dyes may also be used as sun protection in vehicles and living spaces in the form of windows, protective baffles, covers, roofs, or the like.

To produce such photochromic objects, the inventive photochromic benzo[f]chromene dyes may be applied to or embedded in a polymer material, such as an organic synthetic resin material, by various methods described in the prior art, for instance in WO 99/15518.

A distinction is drawn between so-called mass dyeing and superficial dyeing processes. A mass dyeing process comprises, for instance, dissolving or dispersing of the photochromic compound or compounds according to the present invention in a synthetic resin material, e.g., by adding the photochromic compound(s) to a monomer material before polymerization takes place. Another option to produce a photochromic object is to allow the photochromic compound(s) to penetrate the synthetic resin material(s) by dipping the synthetic resin material into a hot solution of the photochromic dye(s) according to the present invention or, for instance, to use a thermotransfer process. The photochromic compound(s) can, for instance, also be provided in the form of a separate layer between adjacent layers of the synthetic resin material, e.g., as part of a polymer film. It is also possible to apply the photochromic compound(s) as part of a coating that is applied to the surface of the synthetic resin material. The term "penetration" should be understood as the migration of the photochromic compound(s) into the synthetic resin material, e.g., by the solvent-supported transfer of the photochromic compound(s) into a polymer matrix, vapor phase transfer or other similar surface diffusion processes.

Advantageously, such photochromic objects, e.g., eyeglasses, can be produced not only by means of the usual mass dyeing process but also by means of superficial dyeing. In the latter variant, a surprisingly low migration tendency can be achieved. This is advantageous particularly in subsequent processing steps since, for instance, in an antireflective coating, film peeling and similar defects can be drastically reduced due to the reduced back diffusion in the vacuum.

Overall, based on the inventive photochromic h-annellated benzo[f]chromene derivatives, any compatible (compatible in chemical respects as well as in color) colorations, i.e., dyes, can be applied to or embedded in the synthetic resin material to satisfy both esthetic considerations as well as medical or fashion aspects. The specifically selected dye(s) can consequently vary as a function of the intended effects and requirements.

The inventive photochromic h-annellated benzo[f] chromene derivatives having the general formula (I) or (II) and (III) can, for instance, be produced using the reaction scheme shown in FIG. 1.

Starting with suitably substituted phenyl acetic acid esters, an ester condensation with cyclic aromatic-aliphatic ketones is carried out using potassium methylate as base (see step i) in FIG. 1). The substituted cyclic aromatic-aliphatic 2-phenylacetyl ketones obtained in step i) are subsequently converted to substituted annellated 2-naphthol derivatives in step ii) in an intramolecular cyclization by means of phosphoric acid. After protecting the naphthol hydroxy group as tert-butyl diphenylsilyl ether (step iii)), the (substituted) amino group required for long-wave absorption is introduced on the naphthalene system by means of palladium catalyzed amination (step iv)). The starting compounds required for this in step iv) carry either a bromine atom or a triflate group as radicals $R_1$ or $R_2$, which may either be present from the start, i.e., in the phenyl acetic acid ester used as starting material in step i), or may be conventionally introduced prior to amination. After splitting off the protective silyl ether group in step v), the substituted annellated 2-naphthol derivatives thus obtained are converted into the inventive compounds with suitable substituted 2-propyne-1-ol derivatives in accordance with step vi).

What is claimed is:

1. A photochromic h-annellated benzo[f]chromene compound corresponding to formula (I):

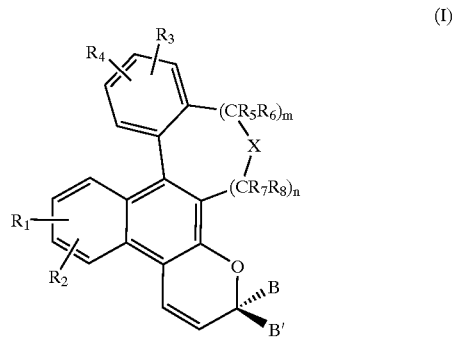

(I)

wherein n and m independently represent 0, 1 or 2, $R_1$, $R_2$, $R_3$ and $R_4$ each independently represent a substituent selected from:

the group α consisting of a hydrogen atom, a ($C_1$–$C_6$) alkyl radical, a ($C_3$–$C_7$) cycloalkyl radical which may contain one or more heteroatoms, a ($C_1$–$C_6$) alkoxy radical, a hydroxy group, a trifluoromethyl group, bromine, chlorine and fluorine;

the group β consisting of an unsubstituted, monosubstituted or disubstituted phenyl, phenoxy, benzyl, benzyloxy, naphthyl or naphthoxy radical, wherein any substituents are selected from the group □ and phenyl;

the group χ wherein $R_1$ and $R_2$ or $R_3$ and $R_4$ form an —A—$(CH_2)_k$—B— group bound to the aromatic ring, wherein k =1 or 2, and A and B are independently selected from the group consisting of oxygen, sulfur, $CH_2$, $C(CH_3)_2$ or $C(C_6H_5)_2$, and wherein a benzo ring may in turn be annellated to the —A—$(CH_2)_k$—B— group;

the group δ consisting of an unsubstituted, monosubstituted or disubstituted amino group, wherein any amine substituents are selected from a ($C_1$–$C_6$) alkyl radical, a ($C_3$–$C_7$) cycloalkyl radical, a phenyl or benzyl radical unsubstituted or substituted with one or more substituents from the group α, an N-morpholine group, an N-thiomorpholine group, an N-piperidine group, an N-azacycloheptane group, an N-piperazine group, an N-(N'-($C_1$–$C_6$-alkyl) piperazine group, an N-pyrrolidine group, an N-imidazolidine group, an N-pyrazolidine group, an N-aziridine group, an N-azetidine group, an N-indoline group, an N-carbazole group, an N-phenothiazine group, an N-phenazine group, an N-phenoxazine group, an N-tetrahydroquinoline group, and an N-tetrahydroisoquinoline group;

the group ε, wherein $R_1$ and $R_2$, or $R_3$ and $R_4$, respectively, together form a —D—$(CH_2)_k$—E— group bound to the benzo ring, wherein k=1 or 2; D is independently selected from the group consisting of $N(CH_3)$ and $N(C_6H_5)$, and E is independently selected from the group consisting of oxygen, sulfur, $CH_2$, $C(CH_3)_2$, $C(C_6H_5)_2$, $N(CH_3)$ and $N(C_6H_5)$, and wherein a benzo ring may in turn be annellated to the —D—$(CH_2)k$—E-group; and the group φ wherein $R_1$ and $R_2$ or $R_3$ and $R_4$, respectively, together with the benzene ring to which they are bound, form a julolidinyl moiety;

provided that at least one of $R_1$, $R_2$ $R_3$ and $R_4$ or $R_1/R_2$ and $R_3/R_4$ is selected from the groups δ, ε and φ;

$R_5$, $R_6$, $R_7$ and $R_8$ are each independently selected from the group α and phenyl, or $R_5$ and $R_6$ together with $R_3$ of a directly adjacent benzo ring form an unsubstituted, monosubstituted or disubstituted benzo or pyrido ring annellated thereto, wherein any substituents are selected from the group α and phenyl, or if m or n is 2, directly adjacent radicals $R_5$ and $R_6$ of two adjacent $CR_5R_6$ units or directly adjacent radicals $R_7$ and $R_8$ of two adjacent $CR_7R_8$ units together form an annellated, unsubstituted, monosubstituted or disubstituted benzo or pyrido ring wherein any substituents are selected from the group α and phenyl, or $R_5$ and $R_6$ and/or $R_7$ and $R_8$ together represent a ($C_3$–$C_7$) cycloalkyl radical, which may contain one or more heteroatoms, and wherein a benzo ring may be annellated to the cycloalkyl radical;

X is selected from the group consisting of O, S, $CR_9R_{10}$ and $NR_{11}$, wherein $R_{11}$ is hydrogen, cyano, ($C_1$–$C_6$) alkyl, ($C_3$–$C_7$) cycloalkyl or phenyl, and $R_9$ and $R_{10}$ are independently selected from the group α and phenyl, or together represent a ($C_3$–$C_7$) cycloalkyl radical, which may contain one or more heteroatoms, or if X is $CR_9R_{10}$, $R_9$ and $R_{10}$ together with the radicals $R_5$ and $R_6$ or $R_7$ and $R_8$ of a directly adjacent $CR_5R_6$ or $CR_7R_8$ moiety may also represent an unsubstituted, monosubstituted or disubstituted benzo or pyrido ring annellated to the X—$C(R_5R_6)$ or X—$C(R_7R_8)$ bond, wherein any substituents are selected from the group α and phenyl;

B and B' are each independently selected from
  the group a) consisting of monosubstituted, disubstituted or trisubstituted aryl radicals selected from the group consisting of phenyl and naphthyl;
  the group b) consisting of unsubstituted, monosubstituted and disubstituted heteroaryl radicals selected from the group consisting of pyridyl, furanyl, benzofuran-2-yl, benzofuran-3-yl, thienyl, benzothieno-2-yl, benzothieno-3-yl, and julolidinyl;
  wherein any substituents on the aryl or the heteroaryl radicals in a) and b) are selected from the groups α, β or δ or two directly adjacent substituents together form a —D—$(CH_2)_k$—E— group bound to the benzo ring as defined above,
  the group c) consisting of structural units having either of the following formulas (V) or (W):

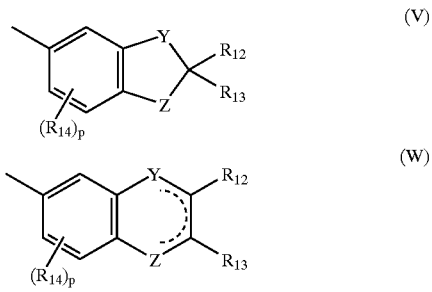

wherein
  Y and Z are independently selected from the group consisting of O, S, CH, $CH_2$ and $NR_{11}$; $R_{11}$ is as defined above;
  $R_{12}$ and $R_{13}$ independently represent hydrogen or a ($C_1$–$C_5$) alkyl radical,
  $R_{14}$ is a substituent selected from the group α, and
  p is 1, 2, or 3;
provided that, if Y in formula (V) is $NR_{11}$, Z is carbon, and
  the group d) wherein B and B' together form an unsubstituted, monosubstituted or disubstituted fluorene-9-ylidene radical or a saturated hydrocarbon radical, which is $C_3$–$C_{12}$ spiro-monocyclic, $C_7$–$C_{12}$ spiro-bicyclic or $C_7$–$C_{12}$ spiro-tricyclic, wherein any fluorene substituents are selected from the group α.

2. A photochromic benzo[f]chromene compound according to claim 1, wherein the cycle or heterocycle annellated according to formula (I) in the h-position of the benzo[f] chromene system is a five-membered ring, a six-membered ring or a seven-membered ring.

3. A photochromic benzo[f]chromene compound according to claim 1, corresponding to formula (II) or formula (III):

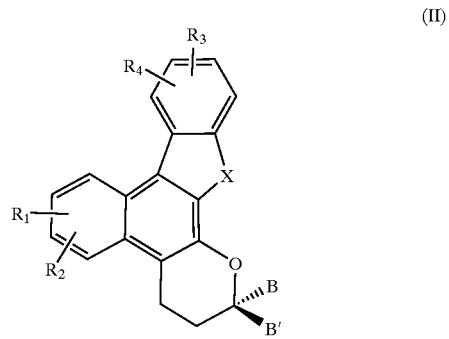

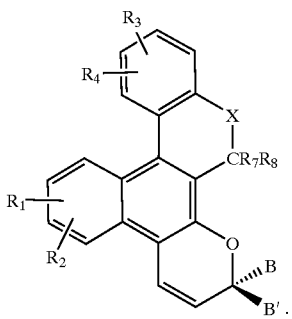

(III)

4. A photochromic benzo[f]chromene compound according to claim 1, wherein $R_1$, $R_2$ $R_3$ and $R_4$ are selected from the groups α, β, and δ, and at least one of $R_1$, $R_2$, $R_3$ and $R_4$ is selected from the group δ.

5. A photochromic benzo[f]chromene compound according to claim 4, wherein at least one of $R_1$ and $R_2$ is selected from the group δ.

6. A photochromic benzo[f]chromene compound according to claim 5, wherein $R_1$ is selected from the group δ and is bound in the 7-position of the h-annellated 2H-benzo[f]chromene ring system.

7. A photochromic benzo[f]chromene compound according to claim 6, wherein the substituent from the group δ is an unsubstituted, monosubstituted or disubstituted amino group, wherein any amine substituents are selected from the group consisting of ($C_1$–$C_6$) alkyl radicals, ($C_3$–$C_7$) cycloalkyl radicals, phenyl or benzyl radicals unsubstituted or substituted with one or more substituents from the group α, an N-morpholine group, an N-piperidine group, an N-azacycloheptane group, an N-piperazine group, an ($C_1$–$C_6$-alkyl)piperazine group, an N-pyrrolidine group, an N-imidazolidine group or an N-pyrazolidine group.

8. A photochromic benzo[f]chromene compound according to claim 1, wherein $R_5$, $R_6$, $R_7$ and $R_8$ are each independently selected from the group α.

9. A photochromic benzo[f]chromene compound according to claim 1, wherein X is O, $CR_9R_{10}$ or $NR_{11}$.

10. A photochromic benzo[f]chromene compound according to claim 1, wherein said compound is selected from the group consisting of:

7-dimethylamino-6-methoxy-2-(4-(N-morpholinyl)phenyl)-2-phenyl-2H, 13H-indeno[1,2-h]benzo[f]chromene, 7-dimethylamino-6-methoxy-2-(4-(N-morpholinyl)phenyl)-2,13,13-triphenyl-2H, 13H-indeno[1,2-h]benzo[f]chromene, 7-dimethylamino-6-methoxy-2-(4-(N-morpholinyl)phenyl)-2-phenyl-2H-13,14-dihydro-naphtho[1,2-h]benzo[f]chromene, 7-dimethylamino-6-methoxy-2-(4-(N-morpholinyl)phenyl)-2-phenyl-2H-benzofuro[3,2-h]benzo[f]chromene, 2-(4-dimethylaminophenyl)-6-methoxy-7-(N-piperidinyl)-2-phenyl-2H, 13H-indeno[1,2-h]benzo[f]chromene, 2-(4-dimethylaminophenyl)-6-methoxy-7-(N-piperidinyl)-2,13,13-triphenyl-2H,13H-indeno[1,2-h]benzo[f]chromene, 2-(4-dimethylaminophenyl)-6-methoxy-7-(N-piperidinyl)-2-phenyl-2H-13,14-dihydro-naphtho[1,2-h]benzo[f]chromene, 2-(4-dimethylaminophenyl)-6-methoxy-7-(N-piperidinyl)-2-phenyl-2H-benzofuro[3,2-h]benzo[f]chromene, 2-(4-dimethylaminophenyl)-6-methoxy-7-(N-morpholinyl)-2-phenyl-2H,13H-indeno[1,2-h]benzo[f]chromene, 2-(4-dimethylaminophenyl)-6-methoxy-7-(N-morpholinyl)-2,13,13-triphenyl-2H,13H-indeno[1,2-h]benzo[f]chromene, 2-(4-dimethylaminophenyl)-6-methoxy-7-(N-morpholinyl)-2-phenyl-2H-13,14-dihydro-naphtho[1,2-h]benzo[f]chromene, 2-(4-dimethylaminophenyl)-6-methoxy-7-(N-morpholinyl)-2-phenyl-2H-benzofuro[3,2-h]benzo[f]chromene, 7-methoxy-6-(N-morpholinyl)-2-(4-(N-morpholinyl)phenyl)-2-phenyl-2H,13H-indeno[1,2-h]benzo[f]chromene, 7-methoxy-6-(N-morpholinyl)-2-(4-(N-morpholinyl)phenyl)-2,13,13-triphenyl-2H,13H-indeno[1,2-h]benzo[f]chromene, 7-methoxy-6-(N-morpholinyl)-2-(4-(N-morpholinyl)phenyl)-2-phenyl-2H-13,14-dihydro-naphtho[1,2-h]benzo[f]chromene, 7-methoxy-6-(N-morpholinyl)-2-(4-(N-morpholinyl)phenyl)-2-phenyl-2H-benzofuro[3,2-h]benzo[f]chromene, 2-(4-dimethylaminophenyl)-9-methyl-2-phenyl-2H,9H,15H-7,8-dihydroindeno[1,2-h]benzo[1,4]oxazino[6,7-f]chromene, 2-(4-dimethylaminophenyl)-9-methyl-2,15,15-triphenyl-2H,9H,15H-7,8-dihydroindeno[1,2-h]benzo[1,4]oxazino[6,7-f]chromene, 2-(4-dimethylaminophenyl)-9-methyl-2-phenyl-2H,9H-7,8,15,16-tetrahydronaphtho[1,2-h]benzo[1,4]oxazino[6,7-f]chromene, and 2-(4-dimethylaminophenyl)-9-methyl-2-phenyl-2H,9H-benzofuro[3,2-h]benzo[1,4]-oxazino[6,7-f]chromene.

11. A photochromic article comprising a synthetic resin substrate and an effective photochromic amount of a compound according to claim 1.

12. A photochromic article according to claim 11, wherein said substrate is an ophthalmic lens.

* * * * *